(12) United States Patent
Habara et al.

(10) Patent No.: US 10,126,382 B2
(45) Date of Patent: Nov. 13, 2018

(54) MAGNETIC RESONANCE IMAGING APPARATUS AND ANTENNA DEVICE

(71) Applicant: HITACHI, LTD., Tokyo (JP)

(72) Inventors: Hideta Habara, Tokyo (JP); Shinichiro Suzuki, Tokyo (JP); Yosuke Otake, Tokyo (JP)

(73) Assignee: HITACHI, LTD., Tokyo (JP)

( * ) Notice: Subject to any disclaimer, the term of this patent is extended or adjusted under 35 U.S.C. 154(b) by 699 days.

(21) Appl. No.: 14/440,125

(22) PCT Filed: Oct. 28, 2013

(86) PCT No.: PCT/JP2013/079100
§ 371 (c)(1),
(2) Date: May 1, 2015

(87) PCT Pub. No.: WO2014/073406
PCT Pub. Date: May 15, 2014

(65) Prior Publication Data
US 2015/0285876 A1    Oct. 8, 2015

(30) Foreign Application Priority Data

Nov. 6, 2012    (JP) .................................. 2012-244195

(51) Int. Cl.
*G01R 33/36*    (2006.01)
*A61B 5/055*    (2006.01)
(Continued)

(52) U.S. Cl.
CPC .............. *G01R 33/36* (2013.01); *A61B 5/055* (2013.01); *G01R 33/34* (2013.01);
(Continued)

(58) Field of Classification Search
None
See application file for complete search history.

(56) References Cited

U.S. PATENT DOCUMENTS

| 4,751,464 A | 6/1988 | Bridges |
| 5,557,247 A | 9/1996 | Vaughn |
(Continued)

FOREIGN PATENT DOCUMENTS

| JP | 2008-119091 A | 5/2008 |
| JP | 2010-042251 A | 2/2010 |
(Continued)

OTHER PUBLICATIONS

International Search Report from International Application No. PCT/JP2013/079100 dated Dec. 10, 2013.

*Primary Examiner* — Melissa Koval
*Assistant Examiner* — Nasima Monsur
(74) *Attorney, Agent, or Firm* — Brundidge & Stanger, P.C.

(57) ABSTRACT

In order to provide a technique in which, in the TEM type antenna, the uniformity of sensitivity in the internal portion of the antenna can be maintained with simple configuration, without scarifying the internal space of the antenna, regardless of a size, a shape and a location of a load, and also regardless of locations of the constitutional members of the antenna, the TEM type antenna includes rung conductors which branch out into plural pieces in the middle portion and join into one piece in the two end portions. In other words, the rung conductor having a void space in the middle portion of the rung conductor in the longitudinal direction is provided. The adjacent rung conductors are disposed to be further closer to each other in the middle portion, and to maintain the same distance as that in the related art in the end portion.

11 Claims, 11 Drawing Sheets

(51) Int. Cl.
  G01R 33/345 (2006.01)
  G01R 33/34 (2006.01)
  G01R 33/385 (2006.01)
  G01R 33/54 (2006.01)

(52) U.S. Cl.
  CPC ....... G01R 33/3453 (2013.01); G01R 33/385 (2013.01); G01R 33/54 (2013.01)

(56) References Cited

U.S. PATENT DOCUMENTS

| | | | |
|---|---|---|---|
| 7,688,070 B2 | 3/2010 | Weyers | |
| 2008/0024133 A1* | 1/2008 | Vaughan | G01R 33/34046 324/318 |
| 2008/0315880 A1* | 12/2008 | Habara | G01R 33/34076 324/318 |
| 2010/0253347 A1* | 10/2010 | Habara | G01R 33/3456 324/318 |
| 2010/0253350 A1* | 10/2010 | Huish | G01R 33/34007 324/318 |
| 2013/0293232 A1* | 11/2013 | Boskamp | G01R 33/422 324/318 |

FOREIGN PATENT DOCUMENTS

| | | |
|---|---|---|
| WO | 2011/105143 A1 | 9/2011 |
| WO | 2012/023385 A1 | 2/2012 |

* cited by examiner (a)

(b)

(a)

(b)

MAGNETIC RESONANCE IMAGING APPARATUS AND ANTENNA DEVICE

TECHNICAL FIELD

The present invention relates to a nuclear magnetic resonance imaging (hereinafter referred to as MRI) technique of measuring a nuclear magnetic resonance (hereinafter referred to as NMR) signal from a hydrogen, phosphorus or the like which exists in an object, and of imaging a nuclear density distribution or a relaxation time distribution and the like. The present invention, particularly, to an antenna device that performs at least one of transmitting a high frequency signal and receiving an NMR signal.

BACKGROUND ART

An MRI apparatus emits a high frequency signal which is an electromagnetic wave to an object disposed in a uniform static magnetic field generated from a static magnetic field magnet. Further, the MRI apparatus excites a nuclear spin existing inside the object, receives a nuclear magnetic resonance signal which is an electromagnetic wave generated from the nuclear spin so as to perform a signal processing and thus image the object. The emitting of the high frequency signal and the receiving of the nuclear magnetic resonance signal are performed by a device called an RF antenna or an RF coil which transmits or receives the electromagnetic wave of radio frequency (RF).

When classified in view of a function of the transmission and reception, the RF coils may be generally divided into three categories, that is, a transmission antenna for performing only transmitting, a reception antenna for performing only receiving, and a transmission and reception antenna for performing both transmitting and receiving. In an MRI apparatus for imaging the human body with a static magnetic field intensity of three or less teslas, a combination is commonly used in which a large transmission antenna, generally of a cylindrical shape or a disk-like shape, is combined with a relatively small reception antenna of various shapes such as a sheet-like shape or a cylindrical shape.

Further, when classified in view of shapes, the RF coils may be largely divided into two categories, that is, one called a surface antenna or a local antenna, and another called a volume coil or a volume antenna. The local antenna is mostly configured to have a circular or planar shape and include a sensitivity function in the vicinity of the antenna so that the antenna is used while being contacted with the surface of the object. On the other hand, the volume antenna has a cylindrical shape or a disk-like shape in which two disks are vertically disposed in a row. Therefore, the volume antenna has sensitivity function inside of the cylindrical shape or in the entire portion between two disks and is thus to be used while an object is disposed therein.

As an example of the volume antenna of the cylindrical shape, there are one called a bird case type (see, for example, NPL 1 and PTL 1), and another called a transverse electromagnetic (TEM) type (see, for example, PTL 2 and PTL 3). In these transmission antennas, typically sixteen to thirty two conductors of a rod-like shape called rungs (cross rod or a cross bar of a ladder) are disposed along the side surface of the cylindrical tube to be parallel to the central axis of the cylindrical tube. Such a transmission antenna of the cylindrical shape is used for an MRI apparatus of a so called tunnel type. In the MRI apparatus of the tunnel type, a magnet of a static magnet field of the cylindrical shape is used to form a tunnel into which the object enters while being laid down on a bed, and thus the imaging is performed.

The TEM type antenna as a transmission antenna of the cylindrical shape is mostly used as a volume antenna for a body trunk or a head in an MRI apparatus having a high magnetic field of three or more teslas. In this case, the currents flowing in the above sixteen to thirty two rungs are coupled with each other so as to be used. Further, the number of independent power feeding points (port) is two.

CITATION LIST

Patent Literature

[PTL 1] U.S. Pat. No. 7,688,070
[PTL 2] U.S. Pat. No. 4,751,464
[PTL 3] U.S. Pat. No. 5,557,247

Non Patent Literature

NPL 1: Cecil E. Hayes, et al., "An Efficient, Highly Homogeneous Radiofrequency Coil for Whole-Body NMR Imaging at 1.5T", Journal of Magnetic Resonance (1985) Vol. 63:p. 622-628

SUMMARY OF INVENTION

Technical Problem

Generally, in a TEM type antenna having an N pieces of rungs, there are N/2+1 resonance modes. For example, the TEM type antenna used for an MRI apparatus of three teslas uses resonance modes in the vicinity of 128 MHz. In a case where this TEM type antenna has twenty four rungs, there are thirteen resonance modes, and the frequencies of the resonance modes exist at an interval of approximately 1 MHz to 2 MHz in a range from about 120 MHz to 135 MHz.

Further, the resonance modes are different from each other in the range of a spatial sensitivity. MRI apparatuses use a phenomenon in which a hydrogen nuclear spin is turned around the static magnetic field direction at a specific frequency. Accordingly, it is preferable to maintain uniform sensitivity in the internal space of the antenna as much as possible. The appropriate number of the resonance modes in the TEM type antenna for satisfying this condition is one.

As described above, the TEM type antenna uses the current coupling between adjacent rungs. Recently, in order to assure the internal space for an antenna, the rungs tend to be disposed close to the outside cylindrical shield. In the TEM type antenna, in case where the distance between the rung and the outside cylindrical shield is relatively small compared with a diameter of the entire cylindrical tube, a mirror current flowing close to the rung causes the efficiency of the antenna to be decreased. Therefore, the current coupling between the adjacent rungs also tends to be weakened.

In the TEM type antenna, when a current coupling between the adjacent rungs is weakened, it can be seen that the frequencies of the resonance modes become close to each other. Further, when the frequencies of the resonance modes in the TEM type antenna become close to each other, the degree of mixing sensitivity ranges of the resonance modes of which frequencies are adjacent to each other increases to easily cause a local non-uniformity of sensitivity. Particularly, in a case where an object such as a human body is disposed to be biased to one side in the internal portion of the antenna, a disturbance occurs in the frequencies of the resonance modes in the TEM type antenna when a target matter such as an object or the cable locally approaches closely to the rung due to positional relationships of the reception coil, the cable or the like. Due to such a disturbance, one resonance mode is likely to receive the influence of sensitivity of other resonance modes which have a sensitivity range other than the center of the range.

Further, in the TEM type antenna, when the current coupling between adjacent rungs is weakened, and when a large object enters the internal portion of the antenna, a phenomenon occurs in which a sensitivity of a side that is close to the power feeding point is different from a sensitivity of a side that is remote from the power feeding point. This phenomenon is because the flow of the current is disturbed due to interaction with the object. For this reason, it is necessary to limit a distance from the power feeding point to a predetermined range. Accordingly, two independent power feeding points are not sufficient. Therefore, it may be necessary to add subordinate ports in portions which are at symmetric points with each other and are apart from each other by 180° on the cylindrical tube axis and thus to provide totally four power feeding points of an independent type and a subordinate type arranged in 2+2. Such a phenomenon occurs significantly, particularly, in a case where a distance between a rung of the TEM type antenna and the cylindrical shield disposed in the outside thereof is relatively small compared with a diameter of the entire cylindrical tube.

The present invention is based on the circumstances described above, and an object of the present invention is to provide a technique in which in the TEM type antenna, the uniformity of sensitivity in the internal portion of the antenna can be maintained with simple configuration, without scarifying the internal space of the antenna, regardless of a size, a shape and a location of a load, and also regardless of locations of the constitutional members of the antenna.

Solution to Problem

According to the present invention, in the TEM type antenna, the degree of the current coupling between adjacent rungs is increased, non-uniformity of sensitivity which is caused due to a biased disposition of a load in the internal portion of the antenna and due to magnitude of the load disposed in the internal portion of the antenna can be also reduced. The TEM type antenna includes rung conductors which branch out into plural pieces in a middle portion and join into one piece in end portions. In other words, the rung conductor having a void space in the middle portion of the rung conductor along the longitudinal direction is provided. The adjacent rung conductors are disposed to be further closer to each other in the middle portion, and to maintain the same distance as that of the related art in the end portion.

Advantageous Effects of Invention

According to the present invention, in the TEM type antenna, the uniformity of sensitivity in the internal portion of the antenna can be maintained with simple configuration, without scarifying the internal space of the antenna, regardless of a size, a shape and a location of a load, and also regardless of locations of the constitutional members of the antenna.

DESCRIPTION OF EMBODIMENTS

Hereinafter, the embodiments according to the present invention will be described.

Figure 1:
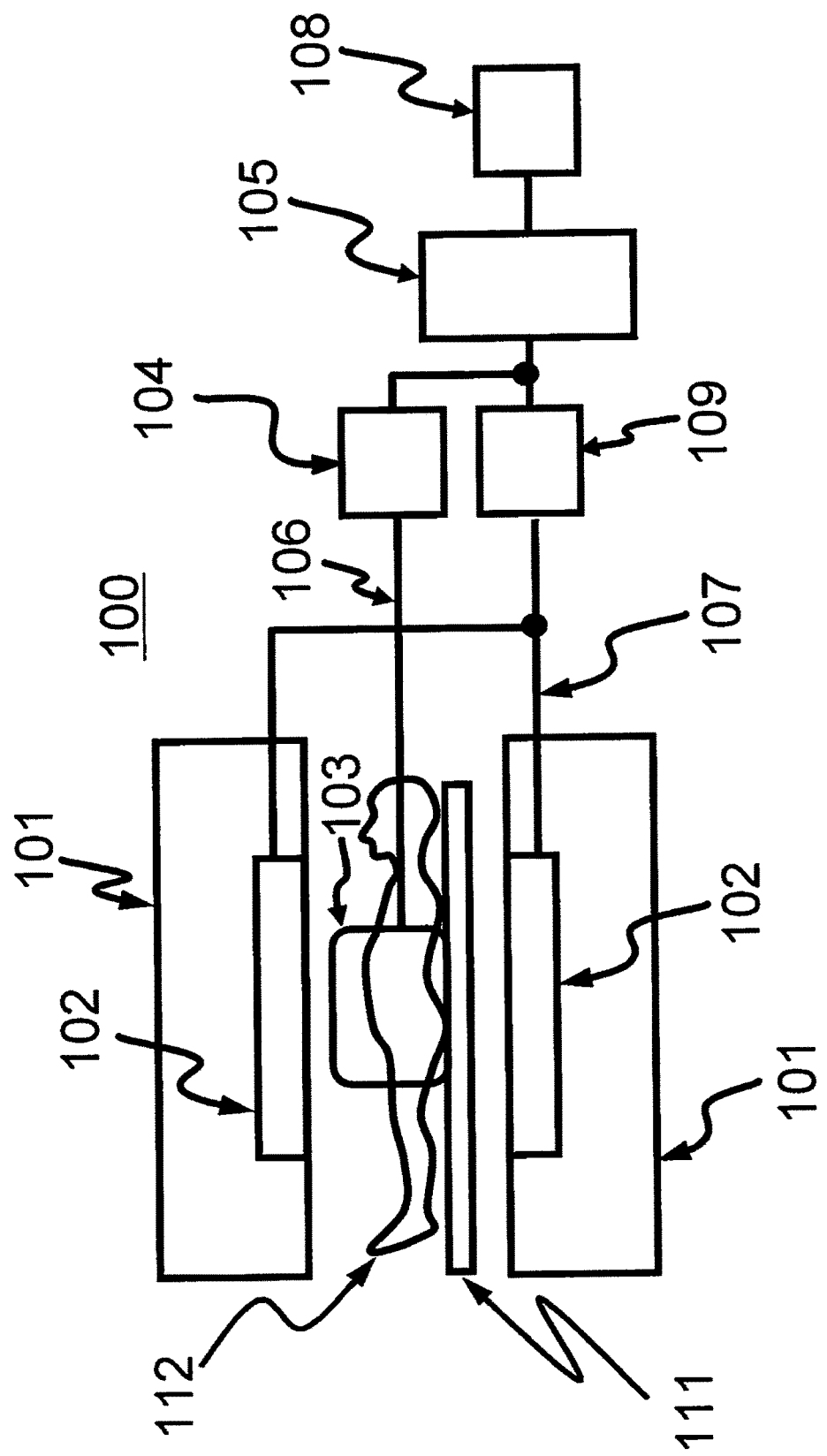
FIG. 1 is a schematic view showing a configuration of an MRI apparatus according to one embodiment of the present invention.

Firstly, a configuration of an MRI apparatus according to the embodiment will be described. FIG. 1 is a schematic view showing a configuration of an MRI apparatus 100 according to the embodiment. The MRI apparatus 100 includes a magnet 101 that forms a static magnetic field in a measuring space in which an object 112 is disposed, a gradient magnetic field coil 102 that provides a magnetic field gradient of a predetermined direction to the static magnetic field, an RF coil 103 that transmits a high frequency signal to the object 112 and receives a nuclear magnetic resonance signal generated from the object 112, a transceiver 104 for preparing a high frequency signal to be transmitted from the RF coil 103 to transmit the high frequency signal to the RF coil 103 and performs signal processing on a nuclear magnetic resonance signal that the RF coil 103 receives, a gradient magnetic field power source 109 that supplies a current to the gradient magnetic field coil 102, a data processing section 105 that controls driving of the transceiver 104 and the gradient magnetic field power source 109, performs various types of information processing, and is operated by an operator, a display device 108 that displays a processing result of the data processing section 105, and a bed 111 on which the object 112 is disposed. The data processing section 105 functions as an imaging section that images internal information of the object 112 based on the nuclear magnetic resonance signal which is received by the RF coil 103 and then on which various types of signal processing are performed by the transceiver 104.

The gradient magnetic field power source 109 and the gradient magnetic field coil 102 are connected to each other through a gradient magnetic field controlling cable 107. Further, the RF coil 103 and the transceiver 104 are connected to each other through a transceiver cable 106 for transmitting and receiving a signal between the RF coil 103 and the transceiver 104. The transceiver 104 includes a synthesizer, a power amplifier, a reception mixer, an analog to digital converter, a receiving-transmitting changeover switch, and the like, all of which are not shown.

The MRI apparatus 100 is classified into a horizontal magnetic field type or a vertical magnetic field type according to a direction of the static magnetic field formed by the magnet 101. In the case of the horizontal magnetic field type, the magnet 101 generally has a cylindrical bore (a central space) to generate the static magnetic field in a horizontal direction of FIG. 1. Whereas, in the case of the vertical magnetic field type, a pair of magnets is disposed vertically with the object interposed between the magnets to generate the static magnetic field in a vertical direction of FIG. 1. The present invention is mainly appropriate to an MRI apparatus of the horizontal magnetic field type.

In the MRI apparatus 100 of the above configuration, the RF coil 103 and the gradient magnetic field coil 102 are used to emit and apply a high frequency signal and a gradient magnetic field which have an intermittent interval of several milliseconds to the object 112 disposed in the static magnetic field, respectively. Further, the object 112 resonates with the high frequency signal to generate a nuclear magnetic resonance signal. Subsequently, the RF coil 103 receives the generated nuclear magnetic resonance signal on which the transceiver 104 and the data processing section 105 perform a signal processing to thereby acquire a magnetic resonance image.

The object 112 may be, for example, a predetermined portion of a human body. The object 112 is laid down on the bed 111 to be disposed in the internal portion of the RF coil 103. The RF coil 103, the gradient magnetic field coil 102 and the bed 111 are disposed inside a space of the static magnetic field formed by the magnet 101.

Further, FIG. 1 shows a single RF coil as the RF coil 103 that transmits the high frequency signal and receives the nuclear magnetic resonance signal, but the present invention is not limited thereto. For example, an RF coil configured to include a plurality of coils such as a combination of a wide-range imaging RF coil and a local-range RF coil may be used as the RF coil 103. Particularly, if not necessarily distinguished, the high frequency signal that the RF coil 103 transmits and the nuclear magnetic resonance signal that the RF coil 103 receives are generally referred to as an electromagnetic wave.

In the embodiment, a TEM type antenna is provided in which about sixteen to thirty two rungs are prepared as the RF coil 103 and thus currents flowing through the rungs are coupled with each other so as to be used. In the TEM type antenna according to the embodiment, non-uniformity of sensitivity which is caused due to a biased disposition of a load in the internal portion of the antenna and due to magnitude of the load disposed in the internal portion of the antenna can be reduced. For this reason, even in a case where a distance between a rung conductor of the antenna and a sheet-like conductor thereof is relatively small, compared with a diameter of the entire cylindrical tube, the efficiency of the antenna is not reduced and also the number of electrical feeding points is only two.

Hereinafter, the RF coil 103 according to the embodiment for realizing the effect mentioned above will be described in detail with the drawings. Herein, an example of an antenna device used as a volume coil for a body trunk will be described as the RF coil 103.

Figure 2:
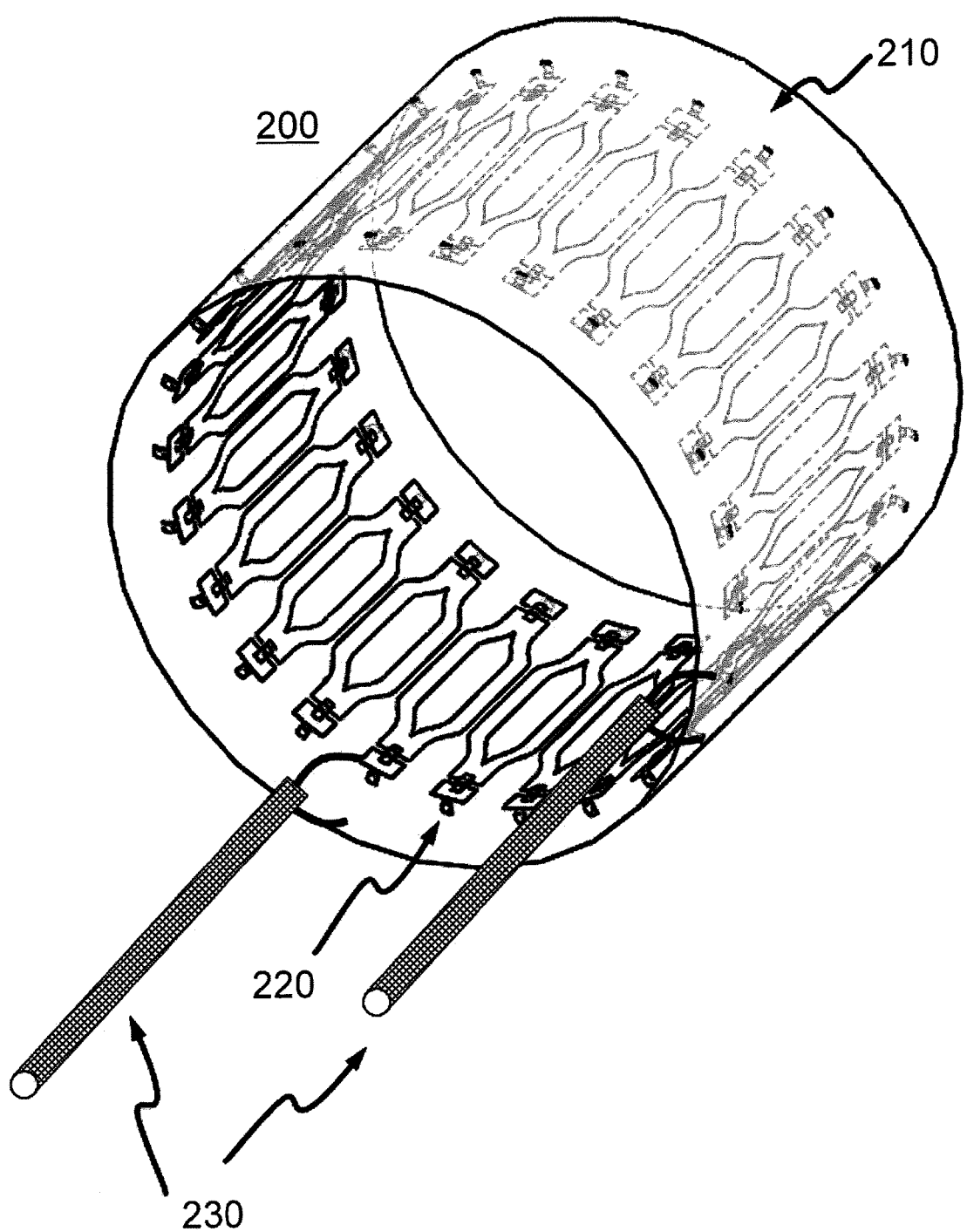
FIG. 2 is a perspective view showing an antenna device according to one embodiment of the present invention.

FIG. 2 is a perspective view showing an antenna device 200 used as the RF coil 103 according to the embodiment.

As shown in FIG. 2, the antenna device 200 of the embodiment is a TEM type antenna which includes a cylindrical sheet-like conductor 210 (hereinafter, referred to as sheet-like conductor) having a function of a ground plane (grounding surface), twenty four sets of rung sections 220, and two power feeding sections 230. As shown in the drawing, the antenna device has a cylindrical shape to be used as the volume coil for a body trunk. Further, the number of the rung sections 220 is not limited thereto.

Hereinafter, in the embodiment, a central axis direction of the cylindrical shape formed by the sheet-like conductor 210 is referred to as an axial direction, a circumferential direction of a circle which is on a sectional area orthogonal to the central axis direction of the cylindrical shape is referred to as a circumferential direction, and a diameter direction of the circle is referred to as a radial direction.

Figure 3:
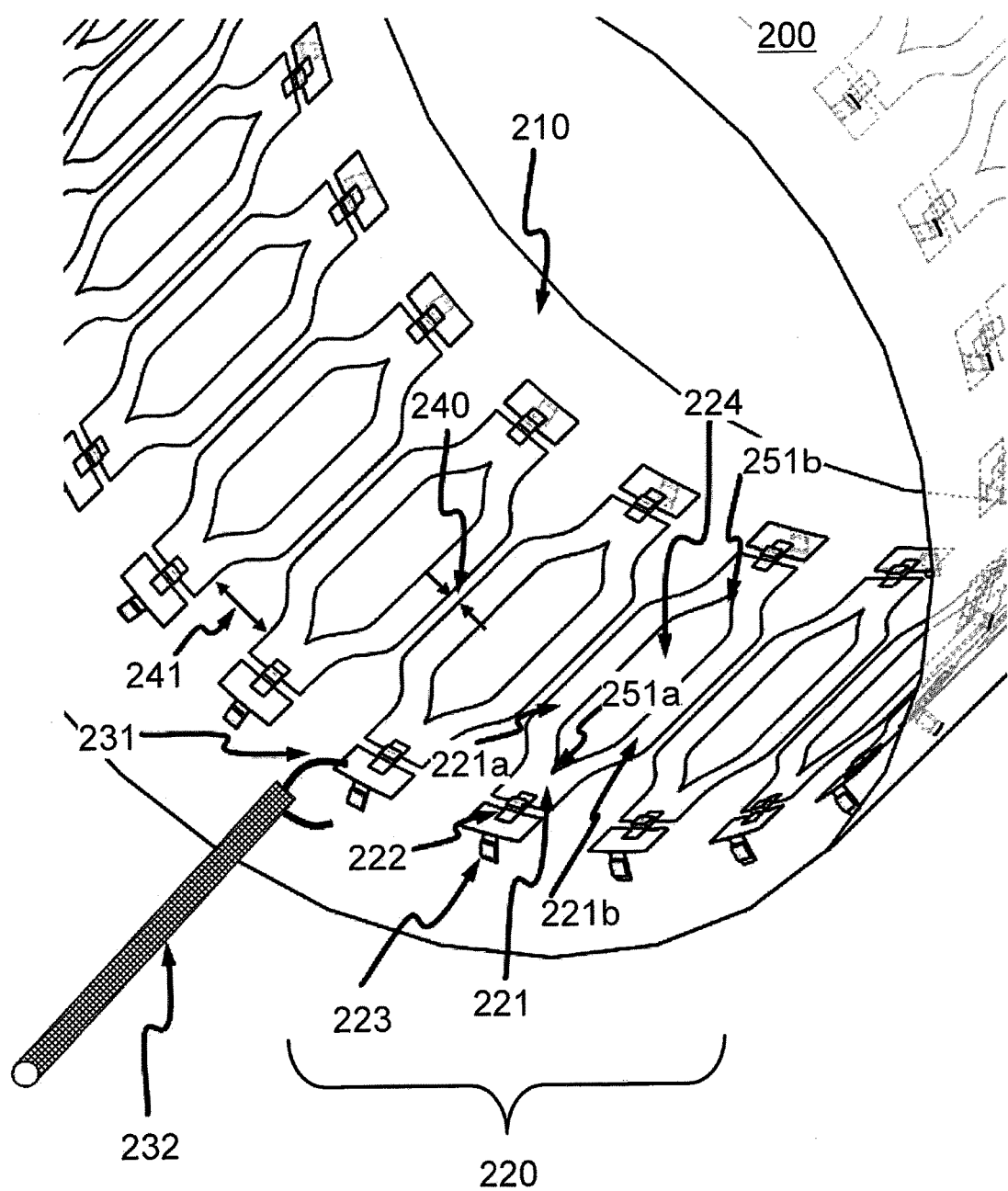
FIG. 3 is an enlarged view showing a part of FIG. 2.

FIG. 3 is an enlarged view showing a part of FIG. 2. As shown in the drawing, the rung section 220 includes a shunt capacitor 223, a rung capacitor 222, and a rung conductor 221.

The rung conductor 221 may be configured to include a conductor which may have a strip shape (thin and long plane or tape-like shape), or a rod shape, or a tubular shape. The rung conductor 221 is disposed on a virtual cylindrical tube surface which is separated from the sheet-like conductor 210 at a predetermined distance (space) on the sheet-like conductor 210 in a side in which the object 112 is disposed. In this case, the conductor is disposed such that the longitudinal direction of the rung conductor becomes the axial direction. As a result, one rung conductor 221 of one rung section 220 is substantially parallel to another rung conductor 221 of another rung section 220 which is adjacent to the one rung section 220. Further, the twenty four sets of rung sections 220 are disposed at a predetermined interval (a gap 241) in the circumferential direction. Further, in a case where the rung conductor 221 is configured to include the conductor of the thin and long planar shape, the plane surface is disposed to be substantially parallel to a surface of the sheet-like conductor 210. In a case where rung conductor is configured to include the tape-like conductor, the tape surface is disposed to be substantially parallel to a surface of the sheet-like conductor 210. This configuration causes the space inside the antenna device 200 to be effectively used and the performance of the antenna device 200 to be improved.

Further, in the embodiment, the gap 241 between adjacent rung conductors 221 becomes reduced, a coupling between the adjacent rung conductors 221 becomes strengthened, and a void space (hole: an opening) 224 is provided on the middle portion of the rung conductor 221 so as to assure a zone through which a magnetic flux passes. As shown in FIG. 3, the rung conductor 221 of the embodiment is configured to include two tape-like (thin and long planar shape) branch rungs 221a and 221b which branch out into two pieces in the vicinity of one end portion, then go along parallel to each other in the middle portion, and finally join each other in the vicinity of the other end. Therefore, the void space (hole) 224 is prepared between a branching site and a joining site of the rung conductor 221, and the width of the middle portion in the circumferential direction is larger than that of the end portion in the circumferential direction.

Hereinafter, in the embodiment, the branching site and the joining site of the rung conductor 221 are commonly referred to as a branching section. In a case where it is necessary to distinguish the two sites from each other, the two are referred to as a first branching section 251a and a second branching section 251b, respectively. Specifically, the rung conductor 221 of the embodiment is configured to include a pair of branching sections 251a and 251b, and plural branch rungs that connect two branching sections constituting the pair of the branching sections. Further, in the embodiment, the widths of the two branch rungs 221a and 221b are identical to each other.

Since the rung conductor 221 of the embodiment includes the void space (hole) 224 in the middle portion, a gap 240 between adjacent rung conductors 221 in the middle portion of the rung section 220 in the axial direction is narrower than that of the gap 241 in the end portion. As a result, a coupling between the adjacent rung conductors 221 becomes strengthened. On the other hand, the void space (hole) 224 is provided in the middle portion to thus assure a zone through which a magnetic flux passes. Further, in the embodiment, an example will be described in which one continuous void space (hole) 224 in the axial direction is provided.

Each of the rung capacitors 222 is inserted into an area of the end portion of the rung conductor 221 in the longitudinal direction. In the embodiment, as shown in FIG. 3, the rung capacitor is inserted into the end portion side from the first branching section 251a and the second branching section 251b. The location of the rung capacitor 222 is used to adjust a continuous length of the rung conductor 221. Therefore, the voltage of the end portion of the rung conductor 221 can be reduced.

The shunt capacitor 223 is inserted into between the sheet-like conductor 210 and the rung section 220. Accordingly, two end portions of the rung conductor 221 are connected to the sheet-like conductor 210 through the shunt capacitor 223.

Herein, the shunt capacitor 223 and the rung capacitor 222 are disposed as one piece for each, but the number of the disposition thereof is not limited to one piece. Two capacitors in parallel (the shunt capacitor 223 and the rung capacitor 222) may be connected to one side of the rung conductor 221 in serial manner to be combined into one piece. Further, the capacitors may be divided into three or more pieces in serial manner.

Further, values of those capacitors (the shunt capacitor 223 and the rung capacitor 222) are adjusted to configure a loop circuit with the rung section 220 and the sheet-like conductor 210, the loop circuit resonating with a frequency of the high frequency signal or the nuclear magnetic resonance signal that the RF coil 103 transmits and receives. Therefore, the antenna device 200 of the embodiment resonates with a frequency of a signal that the RF coil 103 transmits and receives so as to realize a function as an antenna that performs at least one of the receiving and the transmitting.

The power feeding section 230 includes a connecting point 231 and power feeding coaxial cable 232.

The connecting point 231 is a transmission and/or a reception terminal provided in one end of the rung conductor 221 and in the sheet-like conductor 210 just beneath the end. An end portion of the coaxial cable 232 is connected to the connecting point 231. In other words, an internal conductor and an external conductor of the coaxial cable 232 are connected to the rung section 220 side of the connecting point 231 and the sheet-like conductor 210 side thereof, respectively. The coaxial cable 232 is used as the transceiver cable 106 to thus connect the antenna device 200 with the main body (transceiver 104) of the MRI apparatus 100. The antenna device 200 transmits and receives an electromagnetic wave through the coaxial cable 232. Further, the connecting point 231 is also referred to as a transmission and reception terminal, a port of the antenna device 200, a power feeding point and the like. Furthermore, the connecting point 231 is provided for each channel.

Further, the connecting point 231 may be configured to use several lumped constant elements such as capacitor or inductor and thus to have a function as a matching circuit.

Further, even though not shown, the antenna device 200 of the embodiment has a conductor support structure for disposing the rung conductor 221 to be spaced at a predetermined distance from the top of the sheet-like conductor 210.

Figure 4:
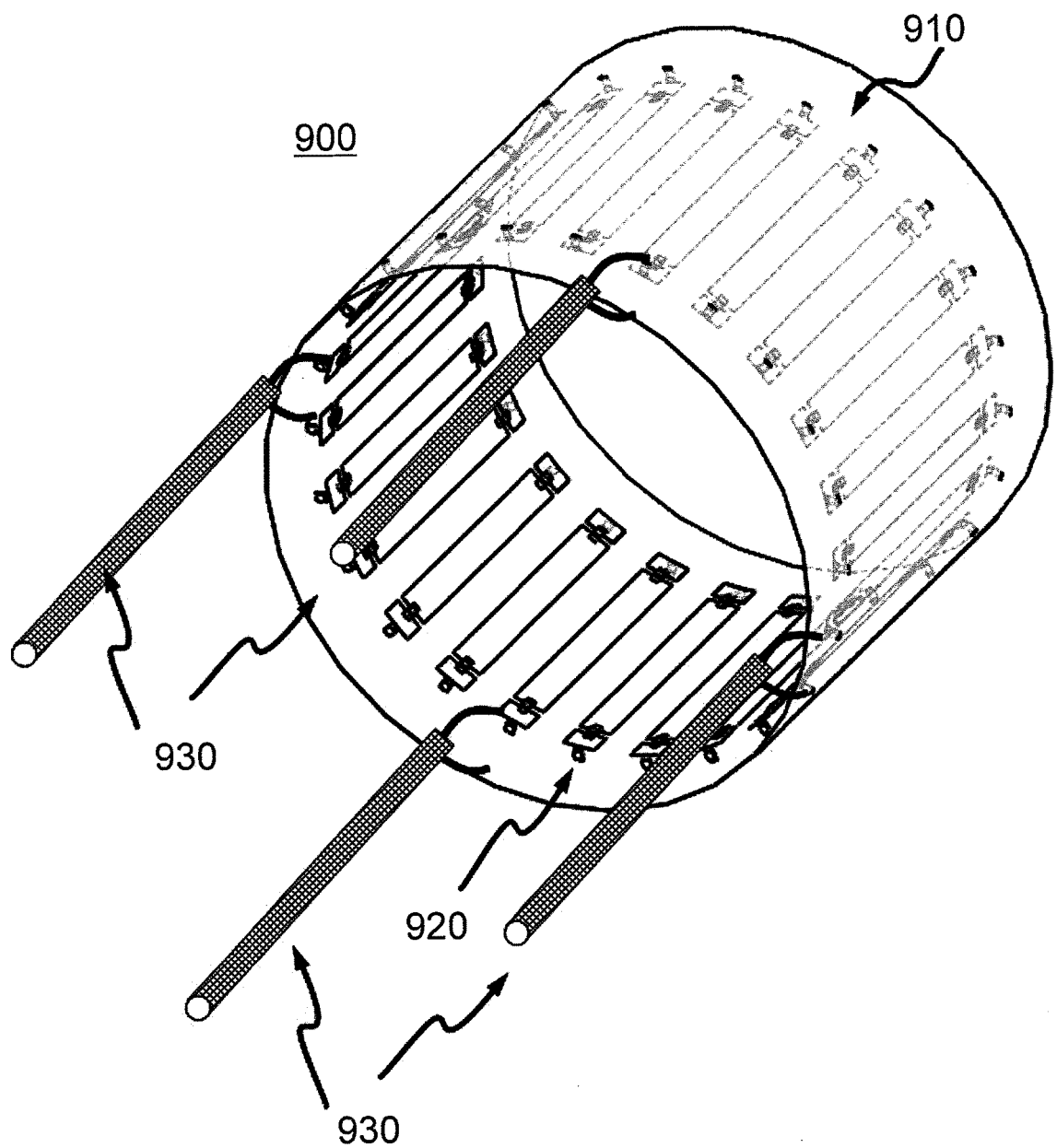
FIG. 4 is a perspective view showing an antenna device according to the related art.

Hereinafter, an RF coil 103 of a related art will be described for comparison. FIG. 4 is a perspective view showing an antenna device 900 according to the related art used as the RF coil 103. As shown in the drawing, the antenna device 900 includes a cylindrical sheet-like conductor 910 (hereinafter, referred to as sheet-like conductor) having a function of a ground plane (grounding surface), twenty four sets of rung sections 920, and two or four power feeding sections 930. FIG. 4 shows an example of a case where four sets of power feeding sections 930 are provided.

Figure 5:
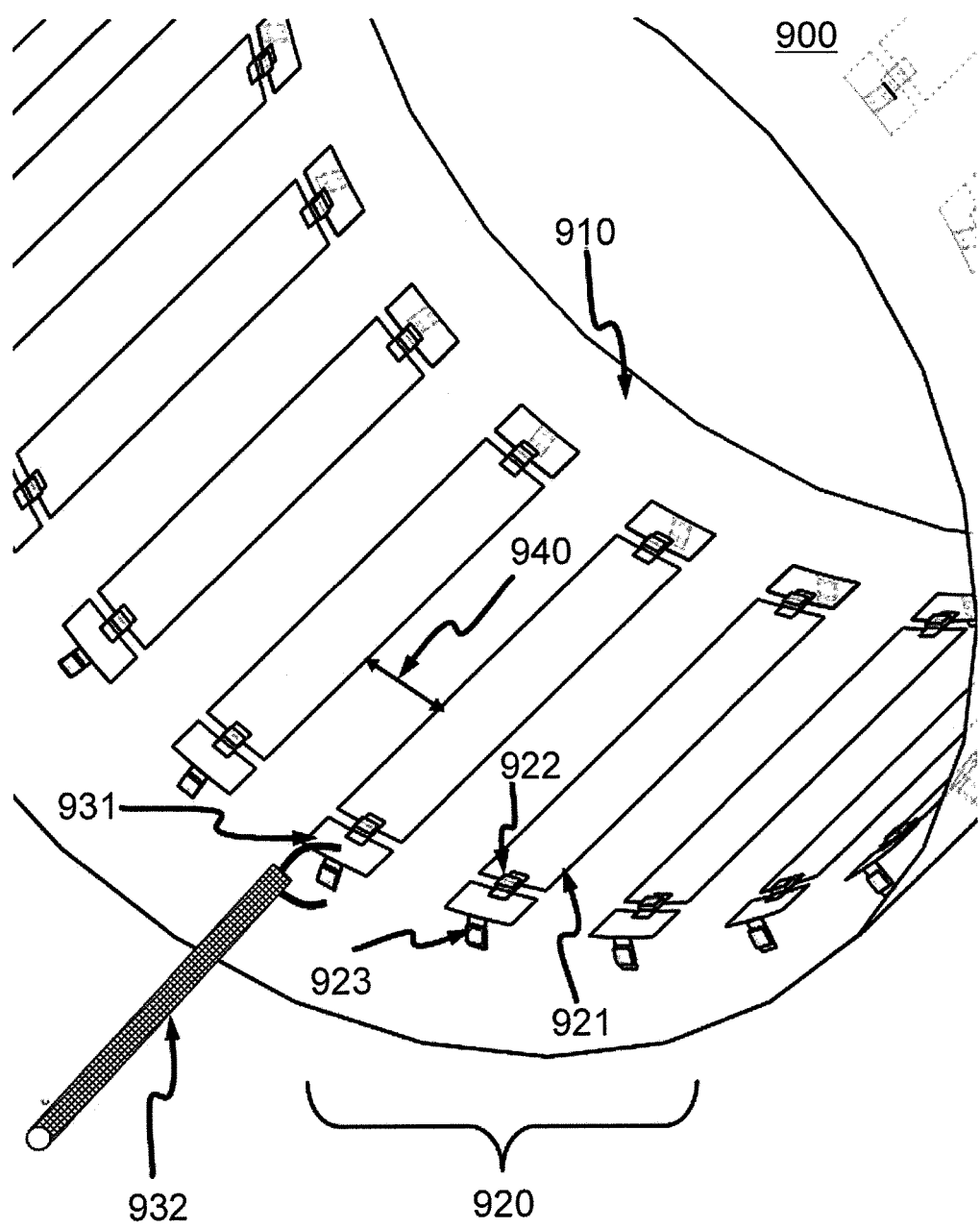
FIG. 5 is an enlarged view showing a part of FIG. 4.

FIG. 5 is an enlarged view showing FIG. 4 in detail. The rung section 920 includes a shunt capacitor 923, a rung capacitor 922, and a rung conductor 921.

The rung conductor 921 is configured to include a conductor which may have a strip shape (thin and long plane or tape-like shape), or a rod shape, or a tubular shape. Disposition thereof is the same as that in the antenna device 200 of the embodiment. However, unlike the antenna device 200 of the embodiment, the rung conductor 921 does not have a void space (hole) in the middle portion. In other words, the rung conductor 921 is configured to include a conductor of the above shape having simply one kind of width. For this reason, a gap 940 between adjacent rung conductors 921 is determined according to a width of the rung conductor 921, a diameter of a cylindrical tube surface on which the rung conductor 921 is disposed, and the number of the rung sections 920.

The configuration and disposition of the shunt capacitor 923 and the rung capacitor 922 are the same as those of the elements of the like name in the antenna device 200 of the embodiment. Further, the power feeding section 930 includes a power feeding point 931 and a power feeding coaxial cable 932 like the antenna device 200 of the embodiment.

When the antenna device 200 of the embodiment shown in FIG. 3 is compared with the antenna device 900 of the related art shown in FIG. 5, the gap 240 between the rung conductors 221 is smaller than the gap 940 between the rung conductors 921. Therefore, in a case where the rung section 220 and the rung section 920 are identical to each other in the number thereof, the current coupling of the rung section 220 in the antenna device 200 of the embodiment becomes strengthened compared with the antenna device 900 of the related art.

Accordingly, in the antenna device 200 of the embodiment, in a case where the number of the rung sections 220 (920) is for example twenty four, diffusion on the frequency axes of thirteen resonance modes increases. Therefore, in the MRI apparatus 100, the stability of the resonance mode used for measuring the nuclear magnetic resonance signal increases.

Therefore, non-uniformity of sensitivity which is caused due to a biased disposition of a load in the internal portion of the antenna device 200 can be suppressed. Further, a non-uniformity of sensitivity which is based on a distance from the power feeding point and is caused due to magnitude of the load disposed in the internal portion of the antenna device 200 can be also suppressed. Therefore, even in a case where the distance between the rung conductor 221 and the sheet-like conductor 210 is relatively small compared with a diameter of a cylindrical tube formed of the sheet-like conductor 210 in the antenna device 200, it is not necessary to increase the number of the power feeding section 230 to four. Since the number of the power feeding section 230 is two, it is possible to meet an irradiation type of high frequency signal referred to as Quadrature Drive (QD) in the simpler manner.

Hereinafter, a simulation will be used to describe that the stability of the resonance mode in the antenna device 200 having the above configuration according to the embodiment further increases, compared with the antenna device 900 of the related art. Herein, a result of the simulation shows that diffusion on the frequency axes of the thirteen resonance modes increased further in the antenna device 200, compared with the case of the antenna device 900.

In the simulation, as the antenna device 200 of the embodiment, the following specification was used. The cylindrical sheet-like conductor 210 was formed of a stainless steel mesh having a diameter of 710 mm, a depth of 1000 mm, and a thickness of 100 microns. The twenty four rung conductors 221 that were provided to be configured to include the tape-like conductor having a width of 40 mm and a length of 400 mm were disposed on a virtual cylindrical tube surface (a conductor support structure) which is spaced at 20 mm away from the sheet-like conductor 210. The rung conductor 221 was cut out in the middle portion thereof to branch out into two tape-like conductors each of which has a width of 20 mm. In this case, the width of the obtained void space (hole) 224 in the circumferential direction had the maximum value of 40 mm. Therefore, the distance (gap) 240 between adjacent rung conductors 221 was approximately 7.7 mm. The capacities of the rung capacitor 222 and the shunt capacitor 223 were 44 pF, respectively. Therefore, the resonance frequency of the antenna device 200 was approximately 122 MHz.

Further, as the antenna device 900 of the related art, the following specification was used. The cylindrical sheet-like conductor 910 was formed of a stainless steel mesh having a diameter of 710 mm, a depth of 1000 mm, and a thickness of 100 microns. The twenty four rung conductors 921 that were provided to be configured to include the tape-like conductor having a width of 40 mm and a length of 400 mm were disposed on a virtual cylindrical tube surface (a conductor support structure) which is spaced at 20 mm away from the sheet-like conductor 910. Therefore, the distance (gap) 940 between adjacent rung conductors 921 was approximately 48 mm. The capacities of the rung capacitor 922 and the shunt capacitor 923 were 44 pF, respectively. Therefore, the resonance frequency of the antenna device 900 was approximately 121 MHz.

As the object 112, a phantom for simulating a living body (not shown) was used. The phantom had a cylindrical shape in which aqueous solution containing water and electrolyte was sealed. The used phantom had a diameter of approximately 30 cm and a length of 50 cm, which reflect the simulation of the human body trunk. The aqueous solution with which the phantom was internally filled had an electric conductivity of 0.66 S/m, and a relative dielectric constant of 77.2. The phantom was provided in the central portion in the internal portion of the antenna device 200 and the antenna device 900, and the simulation was performed.

Figure 6:
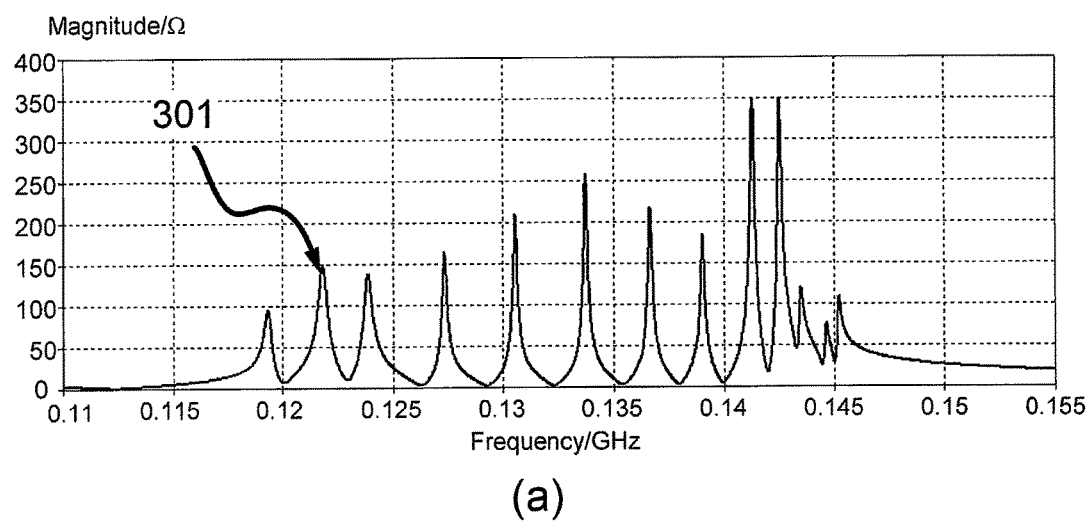
FIG. 6(a) is a graph showing an impedance characteristic indicating a diffusion of a resonance peak in the antenna device according to one embodiment of the present invention.
FIG. 6(b) is a graph showing an impedance characteristic indicating a diffusion of a resonance peak in the antenna device according to the related art.
Figure 6:
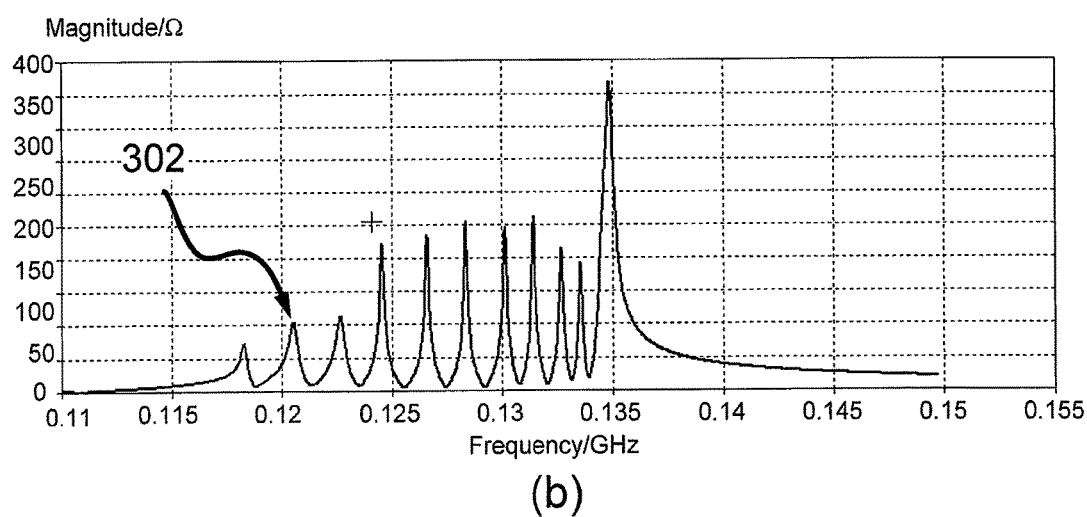

FIG. 6(*a*) is a graph showing an impedance characteristic in the connecting point (a power feeding point) 231 in the antenna device 200 of the embodiment. The horizontal axis indicates a frequency having a range from 0.11 GHz to 0.155 GHz. The vertical axis indicates an absolute value (Magnitude) of the impedance having a range from 0Ω to 400Ω. As shown in the drawing, the impedance characteristic of the antenna device 200 can be seen to have thirteen peaks. The second item from the lowest frequency side, that is, a peak 301 in the vicinity of 0.122 GHz corresponds to the resonance peak used for the MRI. The peak having the lowest frequency was approximately 0.119 GHz. The peak having the highest frequency was approximately 0.145 GHz. The difference thereof was approximately 26 MHz.

On the other hand, FIG. 6(*b*) is a graph showing an impedance characteristic in the connecting point (a power feeding point) 931 in the antenna device 900 of the related art. The horizontal axis indicates a frequency having a range from 0.11 GHz to 0.155 GHz. The vertical axis indicates an absolute value (Magnitude) of the impedance having a range from 0Ω to 500Ω. As shown in the drawing, the impedance characteristic of the antenna device 900 of the related art can be seen to have eleven peaks. It is considered that the reason why the peak number in the related art is different from the peak number of the antenna device 200 shown in FIG. 6 (*a*) is because plural peaks having the highest frequency are overlapped with each other so as to be a single peak. The second item from the lowest frequency side, that is, a peak 302 in the vicinity of 0.121 GHz corresponds to the resonance peak used for the MRI. The peak having the lowest frequency was approximately 0.118 GHz. The peak having the highest frequency was approximately 0.135 GHz. The difference thereof was approximately 17 MHz.

When FIG. 6(*a*) is compared with FIG. 6(*b*), the diffusion (26 MHz) of the resonance peak generated by the antenna device 200 of the embodiment is approximately 1.5 times as much as the diffusion (17 MHz) generated by the antenna device 900 of the related art. Particularly, the high level resonance mode in a higher frequency side is separated from the resonance mode used for the MRI. Therefore, even in a case where the object (a load) 112 is located extremely close to the rung section 220 of the antenna device 200, it can be seen to decrease the possibility that the high level mode is excited and interferes with the mode used for the MRI.

Hereinafter, simulation results will be described for the case of the antenna device 200 of the embodiment and for the case of the antenna device 900 of the related art in which a load is disposed to be biased in the internal portion thereof.

A phantom 113 used as a load was identical to the one mentioned above. In other words, the aqueous solution with which the phantom is internally filled had an electric conductivity of 0.66 S/m, and a relative dielectric constant of 77.2. The phantom 113 had approximately a diameter of 30 cm and a length of 50 cm in size thereof. The phantom 113 is provided to be located in the center in the axial direction and to be biased from the center in the radial direction in the antenna device 200 and the antenna device 900. In other words, the center of a sectional area of the phantom in the radial direction is disposed to be located on a place which is spaced in the radial direction at 17 inches away from a center of a sectional area (a circle) orthogonal to the central axis of the antenna device 200 and the antenna device 900.

Figure 7:
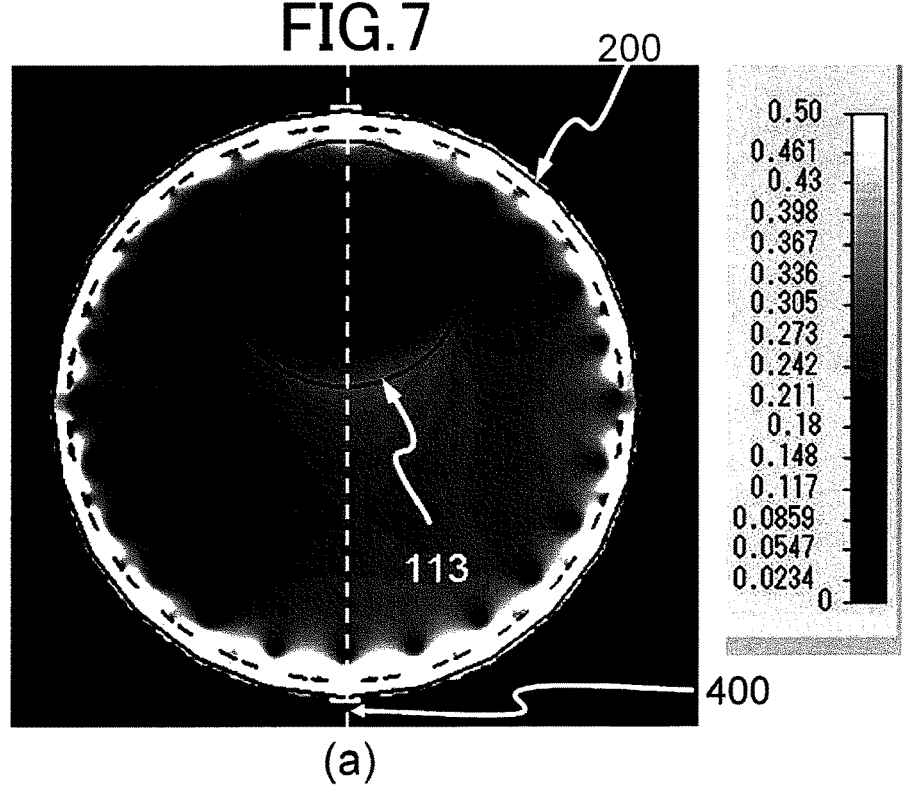
FIG. 7(a) is an explanatory view showing a magnetic field distribution in the antenna device according to one embodiment of the present invention.
FIG. 7(b) is an explanatory view showing a magnetic field distribution in the antenna device according to the related art.
Figure 7:
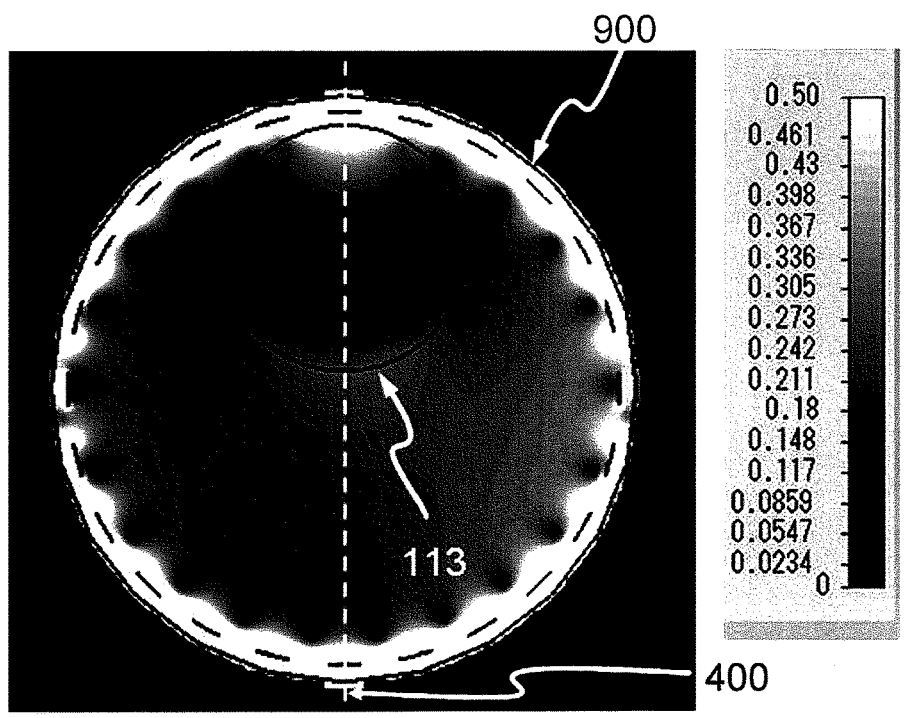

FIG. 7(*a*) and FIG. 7(*b*) show distributions of absolute values for the magnetic field which is generated in this case. FIG. 7(*a*) corresponds to the magnetic field distribution generated in the antenna device 200 of the embodiment, and FIG. 7(*b*) corresponds to the magnetic field distribution generated in the antenna device 900 of the related art. Further, the unit of magnetic field intensity is μT (micro tesla). The magnetic field distribution in an area of the internal portion of the phantom 113 will be described for comparison with reference to FIG. 7 (a) and FIG. 7(b).

In FIG. 7(b), it can be seen that the magnetic field intensity becomes larger in the upper portion of the drawing, and becomes smaller in the central portion of the phantom 113 to thus decrease the uniformity in the internal portion of the area. In other words, according to the antenna device 900 of the related art, it is considered that the phantom 113 is disposed to be asymmetrically located close to the rung section 920 in the internal portion of the antenna device 900 to thus generate the non-uniformity of sensitivity.

On the other hand, regardless of whether or not the phantom 113 is disposed at the same place as that of FIG. 7(b), the case of FIG. 7(a) does not have extremely higher magnetic field intensity in the vicinity of the rung section 220, compared with the case of FIG. 7(b). Accordingly, in the antenna device 200 of the embodiment, even in a case where the phantom 113 is disposed to be asymmetrically located close to the rung section 220, it can be seen that the uniformity of sensitivity in the internal portion of the phantom 113 can be maintained.

Figure 8:
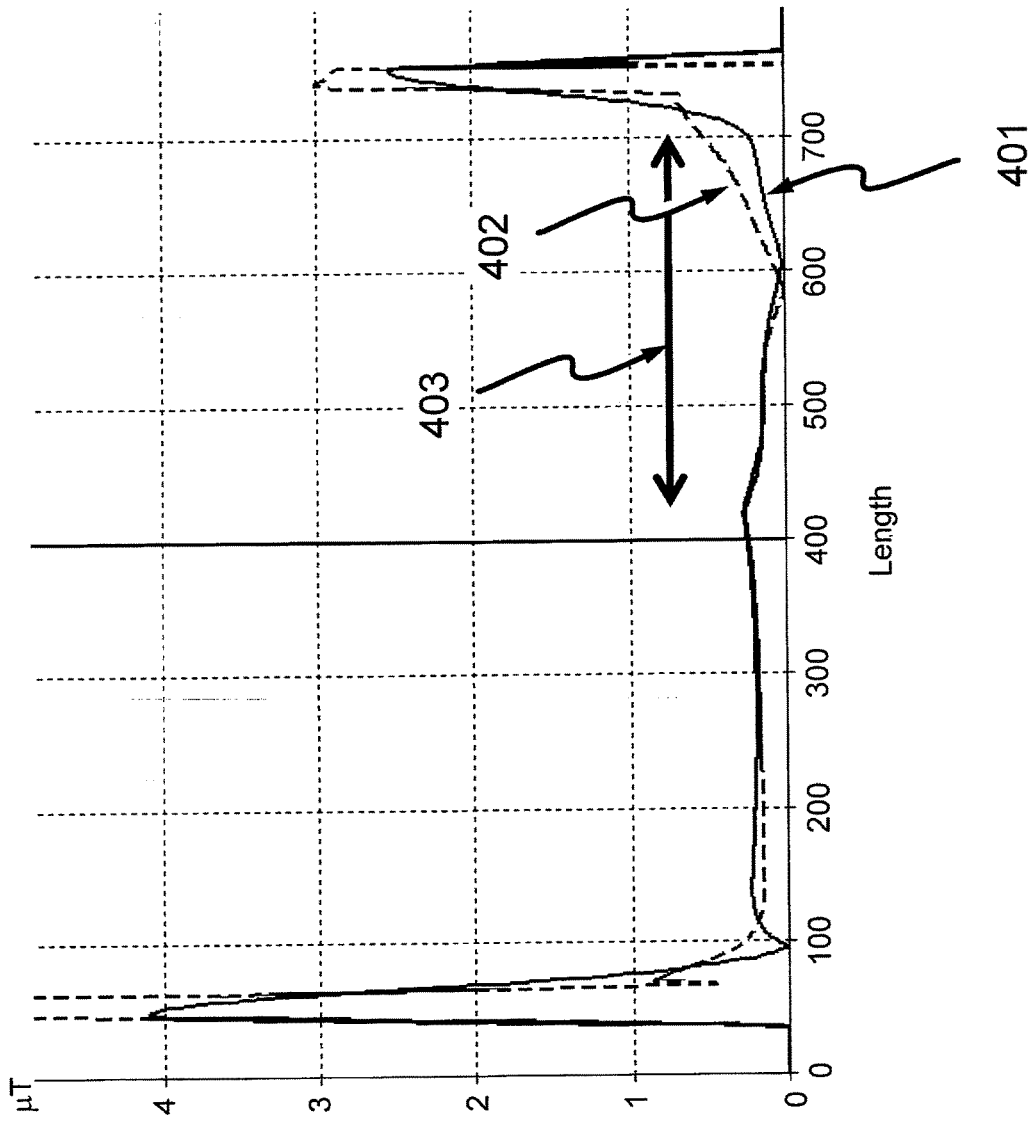
FIG. 8 is a graph showing a absolute value profile of the magnetic field intensity on the line 400 of FIG. 7(a) and FIG. 7(b).

Further, FIG. 8 is a graph of an absolute value profile (a magnetic field profile) of the magnetic field intensity on a line 400 of FIG. 7(a) and FIG. 7(b). The vertical axis indicates the magnetic field intensity (μT), and the horizontal axis indicates a distance (the unit, mm) on the line 400 of FIG. 7(a) and FIG. 7(b), in which the center of the antenna device 200 is set to be 400. A graph 401 of a solid line corresponds to the magnetic field profile of FIG. 7(a), that is, of the antenna device 200 of the embodiment, and a graph 402 of a broken line indicates the magnetic field profile of FIG. 7(b), that is, of the antenna device 900 of the related art. Further, a two-end arrow 403 indicates an area on which the phantom 113 is located.

As shown in the graph 402 in the drawing, it can be seen in the antenna device 900 of the related art that, in the area where the phantom 113 is located, the magnetic field intensity increases in the vicinity of the rung section 220 and the magnetic field distribution, that is, the uniformity of sensitivity is not maintained. On the other hand, as shown in the graph 401, it can be seen in the antenna device 200 of the embodiment that, in the area where the phantom 113 is located, rising of the magnetic field intensity is suppressed even in the vicinity of the rung section 220, and the magnetic field distribution, that is, the uniformity of sensitivity is maintained.

In view of the simulation described above, even in a case where the object is disposed asymmetrically or locally in the internal portion of the antenna, the uniformity of sensitivity is maintained and an excellent sensitivity characteristic can be obtained in the antenna device 200 of the embodiment, unlike in the case of the antenna device 900 of the related art.

Figure 9:
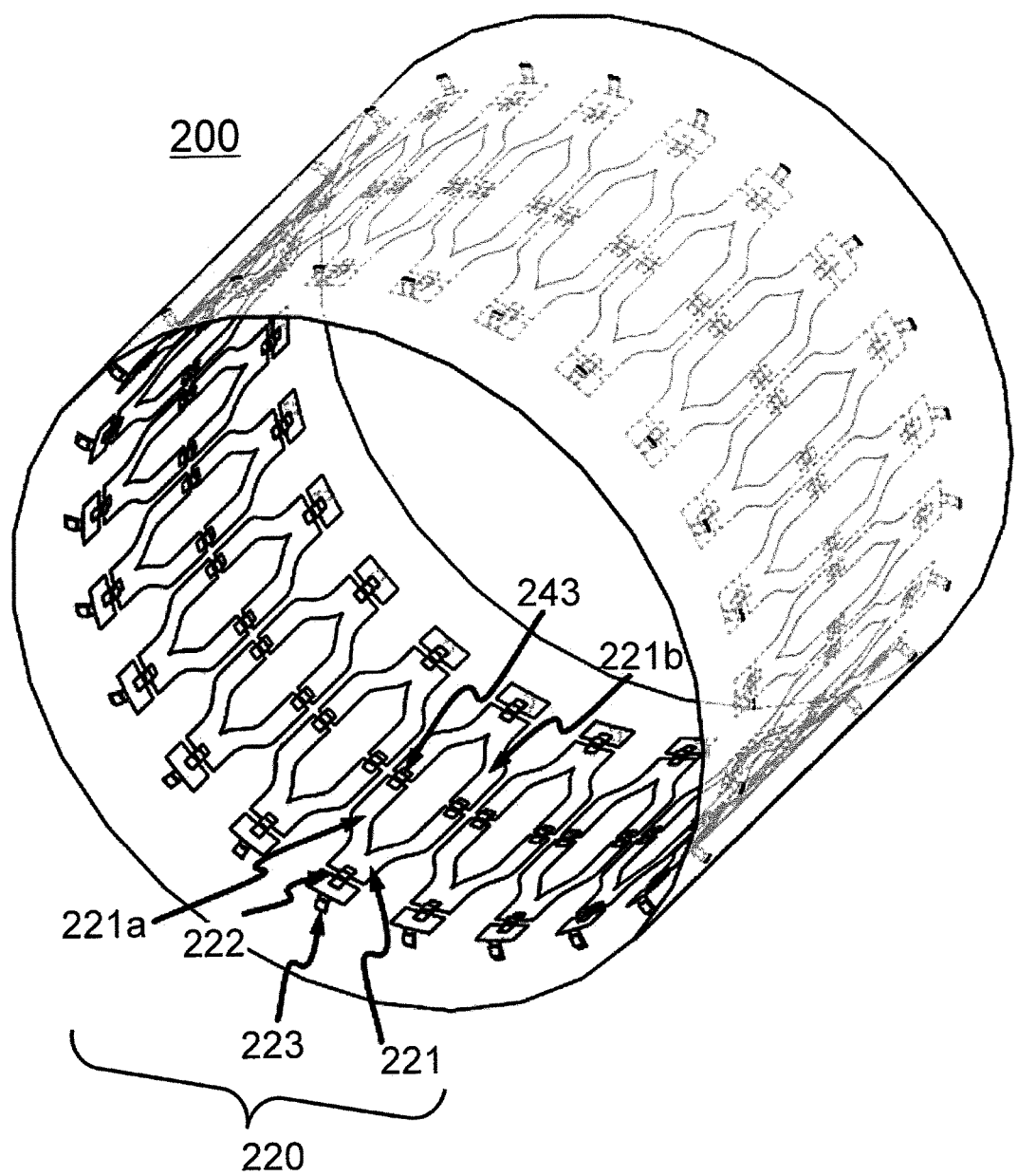
FIG. 9 is a perspective view showing an antenna device according to one modification example of the embodiment of the present invention.

Further, the rung conductor 221 is not limited to the configuration described above. As shown in FIG. 9, for example, a capacitor 243 may be inserted into the branch rungs 221a and 221b. Therefore, each of the branch rungs 221a and 221b is shortened and the voltage of the end portion decreases. Accordingly, it is possible to attain the effect that the emitting of an electric field to a human body is reduced quantitatively. The capacitor 243 may be inserted into any location as long as the insertion location is inside the branch rungs 221a and 221b. Further, the capacitors may be inserted into locations which are different from each other in a distance from each end portion of the branch rung 221a and the branch rung 221b.

Figure 10:
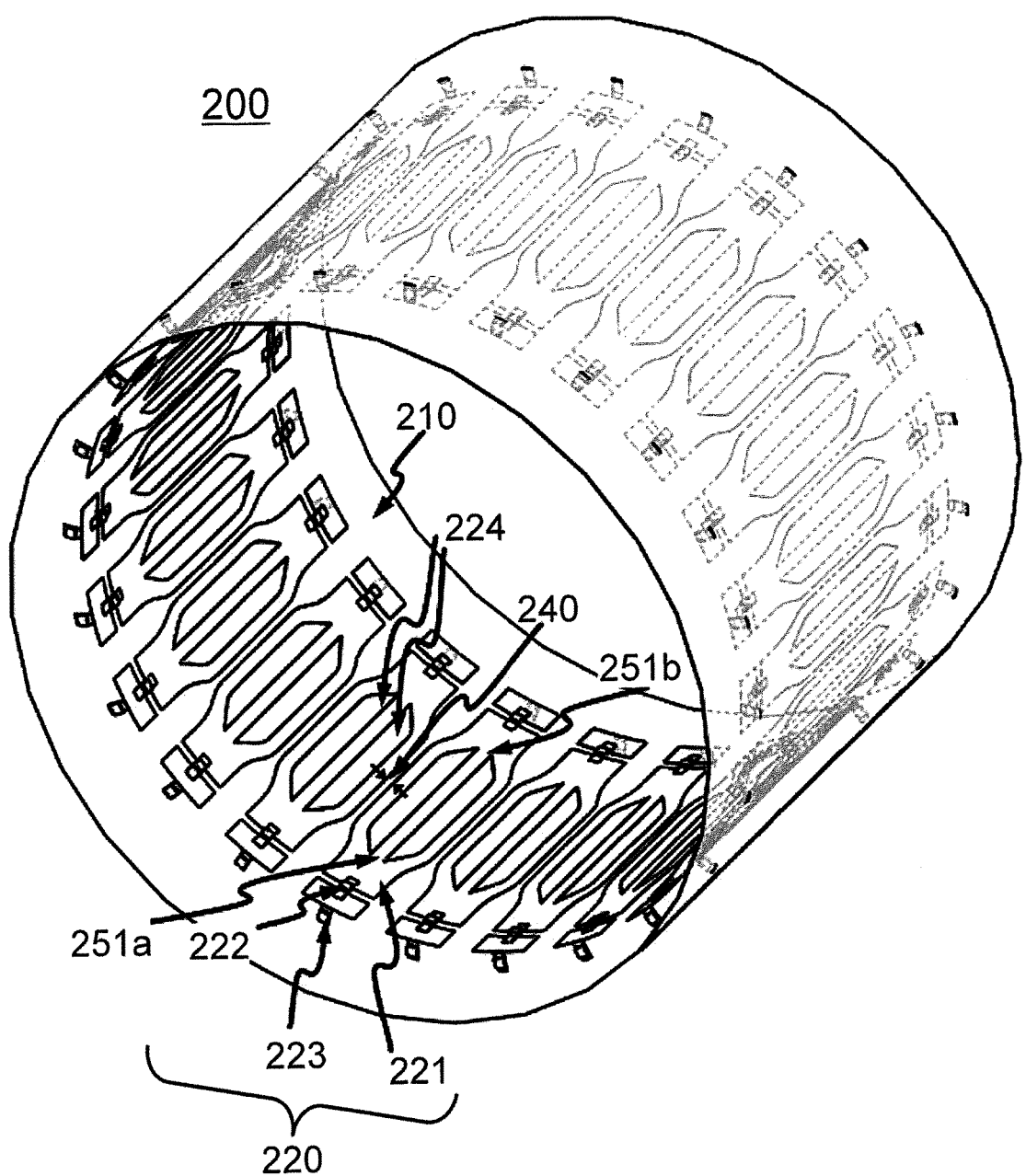
FIG. 10 is a perspective view showing an antenna device according to one modification example of the embodiment of the present invention.

Further, the branch rungs 221a and 221b of the rung conductor 221 are also not limited to two pieces as described above. It is sufficient that the gap 240 between the adjacent rung conductors 221 in the middle portion thereof is smaller than the gap 241 in the end portion while assuring a zone through which a magnetic flux passes. Accordingly, as shown in FIG. 10, for example, the rung conductor 221 may branch out into three pieces in the branching sections 251a and 251b. Two void spaces (holes) 224 are provided in the middle portion of the rung conductor 221. In this case, two branch rungs in the left and right sides in the three-branched rung conductors 221 are disposed closely to the adjacent rung conductor 221 to strengthen the coupling between the adjacent rung conductors 221. Further, the number of the branchings in the branching sections 251a and 251b may be four or more.

However, the number of the void spaces (holes) 224 is not limited to one in the axial direction. In other words, plural sets of the first branching section 251a and the second branching section 251b may be provided in the longitudinal direction of the rung conductor 221.

Figure 11:
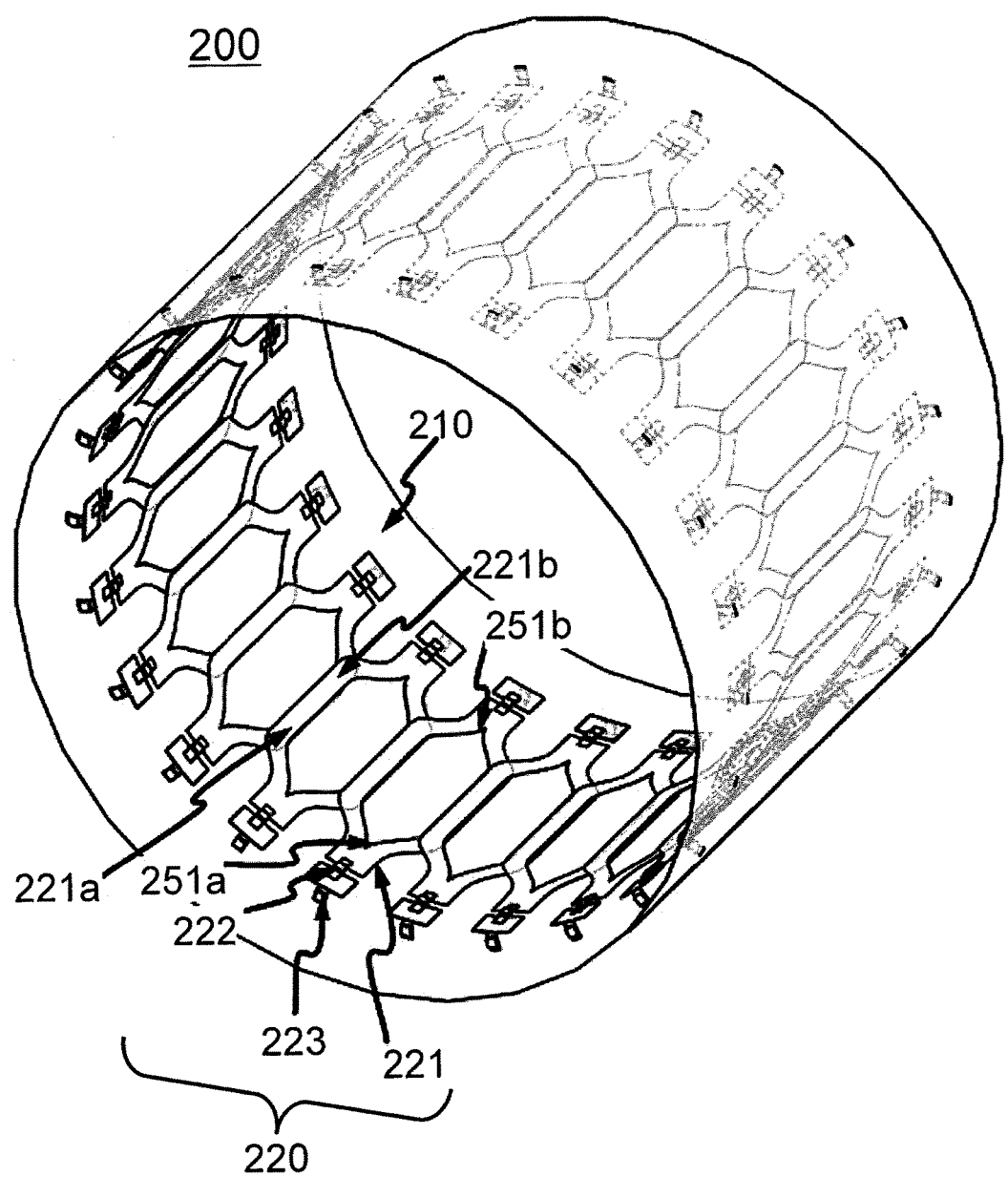
FIG. 11 is a perspective view showing an antenna device according to one modification example of the embodiment of the present invention.

Further, in order to strengthen the coupling between the plural-branched rung conductors 221, as shown in FIG. 11, one branch rung 221a or 221b may be overlapped with at least partly an area of the other branch rung 221a or 221b which is included in the adjacent rung conductor 221 and is located in the closest place to the one branch rung. Therefore, the coupling is further strengthened rather than closely approaching in the circumferential direction and improves the effect thereof. Furthermore, the overlapped portion of the rung conductors 221 is subjected to a necessarily sufficient insulation measure.

Further, in the embodiment, a connecting terminal which is the connecting point 231 between the end portion of the coaxial cable 232 and the antenna device 200 is provided in the vicinity of the end portion of the rung conductor 221 in the one side thereof, as shown in FIG. 2. However, the disposition location of the connecting point (the connecting terminal) 231 is not limited thereto, but for example, may be disposed in the middle portion of the rung conductor 221. In this case, the gap is provided on the middle portion of the rung conductor 221, and the coaxial cable 232 is connected to the two ends of the rung conductor.

Further, the widths of the branch rungs 221a and 221b may not be identical to each other. A branch rung which is closer to the power feeding section 230 may be configured to have a larger size than that of a branch rung which is farther from the power feeding section 230.

Further, the shape of the sheet-like conductor 210 is not limited to the cylindrical shape, but may be an ellipse tubular shape.

Further, it is preferable that the length of the void space (hole) 224 in the axial direction is more than or equal to 60% or less than or equal to 80% of the length of the rung conductor 221 in the axial direction.

As described above, the MRI apparatus 100 of the embodiment includes a magnet 101 that generates a static magnetic field space to form the static magnetic field, and an RF coil 103 that performs at least one of transmitting a high frequency signal into a space of the static magnetic field and receiving a nuclear magnetic resonance signal which is generated from an object disposed inside the static magnetic field. The RF coil 103 includes a sheet-like conductor 210 and plural rung sections 220. The sheet-like conductor 210 has a tubular shape. Each of the plural rung sections 220 includes a rung conductor 221 and capacitors 223 which connect the sheet-like conductor 210 with two end portions of the rung conductor 221, respectively. Each rung conductor 221 of the plural rung sections 220 is disposed in the internal portion of the tubular shape formed by the sheet-like conductor so as to be spaced at a predetermined distance from the sheet-like conductor and to be substantially parallel to an axial direction of the tubular shape, respectively, the axial direction being a longitudinal direction of the tubular shape. The rung conductor 221 is configured to include a void space 224 in a middle portion of the rung conductor and to cause a distance between adjacent rung conductors 221 on the middle portion to be smaller than a distance between adjacent rung conductors on the end portion. The capacitor 223 is adjusted to configure a loop circuit with the rung section 220 and the sheet-like conductor 210, the loop circuit resonating with a frequency of the high frequency signal or the nuclear magnetic resonance signal.

Further, the rung conductor may be configured to have a width of the middle portion in a circumferential direction wider than a width of the end portion in the circumferential direction.

Further, the rung conductor 221 may include a pair of branching sections 251a and 251b and plural branch rungs that extend in the axial direction and connect the pair of branching sections to each other, and the void space 224 may be formed by the pair of branching sections and two adjacent branch rungs.

The number of the branch rungs that the rung conductor 221 includes may be two.

The number of the branch rungs that the rung conductor 221 includes may be three or more.

The rung conductor 221 may include a set of the pair of branching sections.

The rung conductor 221 may include a rung capacitor 222 in a middle portion of the rung conductor 221 in the longitudinal direction.

The rung conductor 221 may have a strip shape.

A branch rung of an end portion among the branch rungs may have an area overlapped in the circumferential direction with a closest branch rung to the branch rung of the end portion, the closest branch rung being one among branch rungs of a rung conductor 221 which is adjacent to the rung conductor 221 that includes the branch rung of the end portion.

The tubular shape may be a cylindrical shape.

As described above, according to the embodiment, in the TEM type antenna device used for the MRI apparatus, the adjacent rung conductors 221 are further closer to each other in the middle portion in the axial direction and thus the current coupling is strengthened. On the other hand, the same gap as that in the related art is maintained in the end portion, and thus the magnetic field coupling is not strengthened. Therefore, according to the antenna device of the embodiment, while the current coupling between the rung conductors 221 is strengthened, the magnetic field coupling can be suppressed, and thus it is possible to increase the diffusion of the frequency of the resonance mode. Therefore, the frequencies of the resonance mode are separated with each other. For this reason, for example, even in a case where a frequency is shifted due to a situation change in the internal portion of the antenna device, an adverse effect such as overlapping with other resonance mode does not occur. Accordingly, it is possible to stabilize the resonance mode which is mainly used.

Further, a distance between the rung conductor of the antenna and the sheet-like conductor can be relatively small, compared with a diameter of the entire cylindrical tube, because the resonance mode is stabilized. Accordingly, it is possible to provide an antenna device having a wider internal space according to the embodiment. Accordingly, it is possible to realize a volume coil for a body trunk having a higher uniformity of sensitivity and a wider internal space for inspection.

Further, since the current coupling increases, even in a case where a large load is disposed in the internal portion of the antenna device, current conductivity is hardly degraded and thus also hardly causes non-uniformity of sensitivity distribution which otherwise would be caused due to the degradation. Therefore, a distance from the power feeding point is mostly not limited to attain sufficient performance even in a case where the number of the power feeding sites is two. Therefore, according to the antenna device of the embodiment, it is possible to attain a desired performance without a complex configuration of the antenna device.

Generally, it is known that if the gap between adjacent rung sections decreases, the current coupling between adjacent rungs is strengthened to improve the performance of the TEM type antenna. However, when the number of the rung section increases, the number of the resonance modes changes. Further, when a width of a single rung section 220 in the circumferential direction increases, the area through which a magnetic flux passes becomes insufficient. According to the embodiment, without such a disadvantageous modification of configuration, it is possible to realize a reducing of the gap between adjacent rung sections.

Therefore, according to the embodiment, it is possible to provide an antenna device in which in TEM type antenna used for the MRI apparatus, the non-uniformity of sensitivity hardly occurs in the internal portion, the wider internal space can be assured and it is not necessary to increase the number of the power feeding sites, regardless of a size and a location of a load.

Further, the antenna device 200 of the embodiment may be a receive-only antenna or a send-only antenna, or a two-way antenna. Further, the antenna device of the embodiment may be applied not only to an RF coil of the MRI apparatus but also applied to all of the apparatuses which use electromagnetic waves having frequencies from several MHz to several GHz.

REFERENCE SIGNS LIST

100 MRI apparatus, 101 Magnet, 102 Gradient magnetic field coil, 103 RF coil, 104 Transceiver, 105 Data processing section, 106 Transceiver cable, 107 Gradient magnetic field controlling cable, 108 Display device, 109 Gradient magnetic field power source, 111 Bed, 112 Object, 113 Phantom, 200 Antenna device, 210 Sheet-like conductor, 220 Rung section, 221 Rung conductor, 221a Branch rung, 221b Branch rung, 222 Rung capacitor, 223 Shunt capacitor, 224 Bore space, 230 Power feeding section, 231 Connecting point, 232 Coaxial cable, 240 Gap, 241 Gap, 243 Capacitor, 251a First branch section, 251b Second branch section, 301 Peak, 302 Peak, 400 Line, 401 Graph, 402 Graph, 403 Two-end arrow, 710 Diameter, 900 Antenna device, 910 Sheet-like conductor, 920 Rung section, 921 Rung conductor, 922 Rung capacitor, 923 Shunt capacitor, 930 Power feeding section, 931 Power feeding point, 932 Power feeding coaxial cable, 940 Gap

The invention claimed is:

1. A magnetic resonance imaging apparatus comprising:
a magnet that generates a static magnetic field space to form the static magnetic field; and
an RF coil that performs at least one of: transmitting a high frequency signal into a space of the static magnetic field or receiving a nuclear magnetic resonance signal which is generated from an object disposed inside the static magnetic field, wherein the RF coil includes:
  a sheet-like conductor, and
  a plurality of rung sections,
wherein the sheet-like conductor has a tubular shape,
wherein each of the plurality of rung sections includes:
  a rung conductor, and
  a plurality of capacitors which connect the sheet-like conductor with two end portions of the rung conductor, respectively,
wherein each rung conductor of the plurality of rung sections is disposed in an internal portion of the tubular shape formed by the sheet-like conductor so as to be spaced at a predetermined distance from the sheet-like conductor and to be substantially parallel to an axial direction of the tubular shape, respectively, the axial direction being a longitudinal direction of the tubular shape,
wherein the rung conductor is configured to include a void space in a middle portion of the rung conductor and to cause a distance between adjacent rung conductors on the middle portion to be smaller than a distance between adjacent rung conductors on the end portion,
wherein the rung conductor includes:
  a pair of branching sections, and
  a plurality of branch rungs that extend in the axial direction and connect the pair of branching sections to each other, and
wherein the void space is formed by the pair of branching sections and two adjacent branch rungs, and
wherein a capacitor of the plurality of capacitors is adjusted to configure a loop circuit with a rung section of the plurality of rung sections and the sheet-like conductor, the loop circuit resonating with a frequency of the high frequency signal or the nuclear magnetic resonance signal.

2. The magnetic resonance imaging apparatus according to claim 1, wherein the rung conductor is configured to have a width of the middle portion in a circumferential direction wider than a width of the end portion in the circumferential direction.

3. The magnetic resonance imaging apparatus according to claim 1, wherein a number of the plurality of branch rungs that the rung conductor includes is two.

4. The magnetic resonance imaging apparatus according to claim 1,
  wherein a number of the plurality of branch rungs that the rung conductor includes is three or more.

5. The magnetic resonance imaging apparatus according to claim 1, wherein the rung conductor includes a set of the pair of branching sections.

6. The magnetic resonance imaging apparatus according to claim 1, wherein the rung conductor includes a rung capacitor in a middle portion of the rung conductor in the longitudinal direction.

7. The magnetic resonance imaging apparatus according to claim 1, wherein the rung conductor has a strip shape.

8. The magnetic resonance imaging apparatus according to claim 1, wherein a branch rung of an end portion among the plurality of branch rungs has an area overlapped in a circumferential direction with a closest branch rung to the branch rung of the end portion, the closest branch rung being one among a second plurality of branch rungs of a second rung conductor which is adjacent to the rung conductor that includes the branch rung of the end portion.

9. The magnetic resonance imaging apparatus according to claim 1, wherein the tubular shape is a cylindrical shape.

10. An antenna device that performs at least one of: transmitting or receiving a predetermined frequency signal, the antenna device comprising:
  a sheet-like conductor; and
  a plurality of rung sections,
  wherein the sheet-like conductor has a tubular shape,
    wherein each of the plurality of rung sections includes:
      a rung conductor, and
      a plurality of capacitors which connect the sheet-like conductor with two end portions of the rung conductor, respectively,
  wherein each rung conductor of the plurality of rung sections is disposed in an internal portion of the tubular shape formed by the sheet-like conductor so as to be spaced at a predetermined distance from the sheet-like conductor and to be substantially parallel to an axial direction of the tubular shape, respectively, the axial direction being a longitudinal direction of the tubular shape,
  wherein the rung conductor is configured to include a void space in a middle portion of the rung conductor and to cause a distance between adjacent rung conductors on the middle portion to be smaller than a distance between adjacent rung conductors on the end portion,
  wherein the rung conductor includes:
    a pair of branching sections, and
    a plurality of branch rungs that extend in the axial direction and connect the pair of branching sections to each other, and
  wherein the void space is formed by the pair of branching sections and two adjacent branch rungs, and
  wherein a capacitor of the plurality of capacitors is adjusted to configure a loop circuit with the rung section and the sheet-like conductor, the loop circuit resonating with a frequency of a high frequency signal or a nuclear magnetic resonance signal.

11. The antenna device according to claim 10, wherein the rung conductor is configured to have a width of the middle portion in a circumferential direction that is wider than a width of the end portion in the circumferential direction.

* * * * *